United States Patent
Johnson et al.

(10) Patent No.: US 9,750,587 B2
(45) Date of Patent: Sep. 5, 2017

(54) POWER TOOTHBRUSH WITH A TUNABLE BRUSHHEAD ASSEMBLY SYSTEM

(71) Applicant: KONINKLIJKE PHILIPS N.V., Eindhoven (NL)

(72) Inventors: Ahren Karl Johnson, North Bend, WA (US); Scott Robert Wills, Seattle, WA (US); Tyler G. Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 14/422,201

(22) PCT Filed: Aug. 31, 2013

(86) PCT No.: PCT/IB2013/058190
§ 371 (c)(1),
(2) Date: Feb. 18, 2015

(87) PCT Pub. No.: WO2014/033685
PCT Pub. Date: Mar. 6, 2014

(65) Prior Publication Data
US 2015/0173874 A1    Jun. 25, 2015

Related U.S. Application Data

(60) Provisional application No. 61/695,377, filed on Aug. 31, 2012.

(51) Int. Cl.
*A61C 17/34* (2006.01)

(52) U.S. Cl.
CPC ........... *A61C 17/3454* (2013.01); *Y10T 29/49* (2015.01)

(58) Field of Classification Search
CPC .................................................. A61C 17/3454
See application file for complete search history.

(56) References Cited

U.S. PATENT DOCUMENTS

| 3,676,218 A | 7/1972 | Sawyer |
| 5,784,742 A | 7/1998 | Giuliani et al. |
| 6,859,968 B2 | 3/2005 | Miller et al. |
| 2006/0101598 A1 | 5/2006 | Fujimoto et al. |

(Continued)

FOREIGN PATENT DOCUMENTS

| CN | 1662190 A | 8/2005 |
| CN | 1775186 A | 5/2006 |
| CN | 201052193 Y | 4/2008 |

*Primary Examiner* — Randall Chin

(57) ABSTRACT

A power toothbrush appliance (10) and a method for tuning a brushhead assembly system (41) thereof. The appliance includes a handle portion (16), a drive assembly and a brushhead assembly system (41). The drive assembly includes a DC motor (34) and an eccentric coupling (46) which drives the brushhead assembly system by means of a yoke mechanism. The brushhead assembly system includes a beam portion (50) which moves laterally about a pivot (47). A brushhead (12) is attachable to and removable from a distal end of the beam. The beam is tunable by changing the stiffness thereof, or the length thereof, or the cross-sectional moment thereof, in order to control the resonant frequency of the brushhead assembly system relative to the drive frequency of the appliance to maintain the amplitude of the brush member within a range of 1.0-2.5 mm, preferably 1.75 mm.

13 Claims, 3 Drawing Sheets

(56) References Cited

U.S. PATENT DOCUMENTS

| | | | |
|---|---|---|---|
| 2006/0168744 A1* | 8/2006 | Butler | A61C 17/222 |
| | | | 15/22.1 |
| 2008/0115300 A1 | 5/2008 | Spooner et al. | |
| 2008/0209650 A1 | 9/2008 | Brewer et al. | |
| 2011/0010875 A1 | 1/2011 | Iwahori et al. | |
| 2012/0156641 A1* | 6/2012 | Wada | A61C 17/0202 |
| | | | 433/82 |

* cited by examiner

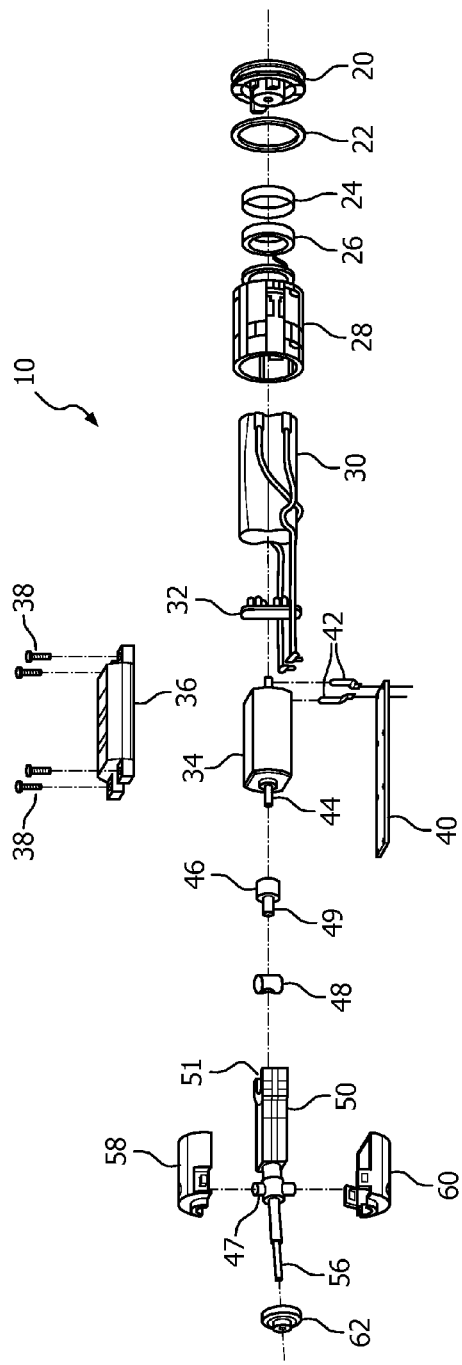
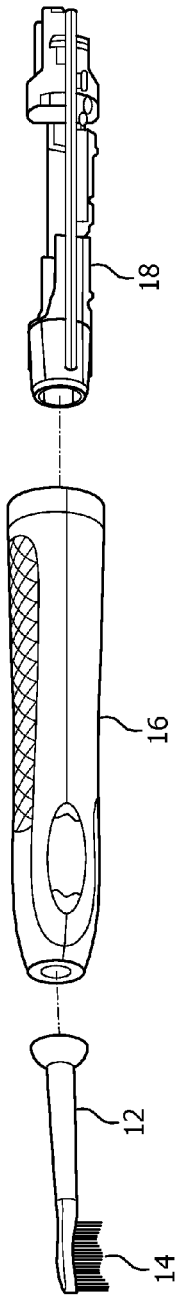
FIG. 1
FIG. 1A

POWER TOOTHBRUSH WITH A TUNABLE BRUSHHEAD ASSEMBLY SYSTEM

CROSS-REFERENCE TO PRIOR APPLICATIONS

This application is the U.S. National Phase application under 35 U.S.C. §371 of International Application No. PCT/IB2013/058190, filed on Aug. 31, 2013, which claims the benefit of U.S. Provisional Patent Application No. 61/695,377, filed on Aug. 31, 2012. These applications are hereby incorporated by reference herein.

TECHNICAL FIELD

This invention relates generally to power toothbrushes having an oscillating brushhead action, and more specifically concerns control of the configuration of a part of the brushhead assembly system for the purpose of maintaining the amplitude of the brushhead action within a desired range.

BACKGROUND OF THE INVENTION

Brushhead assembly systems for power toothbrushes with a back-and-forth, sweeping brush member motion typically include a drive train member (drive beam) and a brushhead with brush member which can together vary in stiffness, center of gravity and mass, all of which affect the resonant frequency of the brushhead assembly system. Because of the relatively thin geometry and the flexible material, typically plastic, used in many such brushheads, the resonant frequency of the brushhead assembly system is frequently between 100-250 Hz, within which range may be the operating/drive frequency of the power toothbrush.

This relationship between the drive frequency of the toothbrush and the resonant frequency of the brushhead assembly system may in some cases be helpful, producing larger sweeping amplitudes with relatively small mechanical driver motion. However, it can also be detrimental if the resonant frequency is too close to the drive frequency, which results in excessive amplitudes of the brush member, i.e. up to 9 mm, which is both difficult to control and potentially harmful to the user.

Hence, there is a need for a brushhead assembly system which includes a portion which can be conveniently tuned so as to shift the resonant frequency of the brushhead assembly system up or down relative to the drive frequency to control the amplitude of brush member movement to be within a desired range. This allows for the use of a larger tolerance range of flexible brushheads, without the necessity of a high degree of control over the manufacture of the various parts of the brushhead assembly system.

SUMMARY OF THE INVENTION

Accordingly, such a power toothbrush comprises: a handle portion (16) which includes a DC motor (34) having a motor shaft (44);an eccentric coupling member (46) mounted on the motor shaft; and a brushhead assembly system (48), which includes a beam member (50) and a removable brushhead (12) to which is mounted a brush member (14), wherein the beam member is mounted for lateral movement about a pivot (47), the lateral movement being accomplished by interaction of the coupling member with a proximal end portion of the beam member, the beam member being arranged and configured such that by tuning one of the following characteristics: (1) the stiffness of the beam, (2) the length of the beam and (3) the cross-sectional moment of inertia of the beam, the resonant frequency of the brushhead assembly system can be changed relative to a drive frequency of the toothbrush that the amplitude of motion of the brush member during operation is maintained within a range of 1.0-2.5 mm.

Further, the method for tuning a brushhead assembly system portion of a power toothbrush to control the resonant frequency thereof, wherein the brushhead assembly system includes a beam portion (50) which is moved by a drive system of the power toothbrush about a pivot (47) and a brushhead (14) attachable to the beam which includes a brush member (14), comprising the steps of: changing one of selected characteristics of the beam so as to maintain a sufficient difference between the resonant frequency of the brushhead assembly system and the drive frequency of the appliance that the amplitude of the brush member in operation is within a range of 1-2.5 mm, wherein the selected characteristics are: (1) stiffness of the beam; (2) length of the beam; and (3) cross-sectional moment of inertia of the beam.

BRIEF DESCRIPTION OF THE DRAWINGS

FIGS. 1 and 1A are exploded views of a power toothbrush incorporating the structure of the present invention.

BEST MODE FOR CARRYING OUT THE INVENTION

Figure 2:
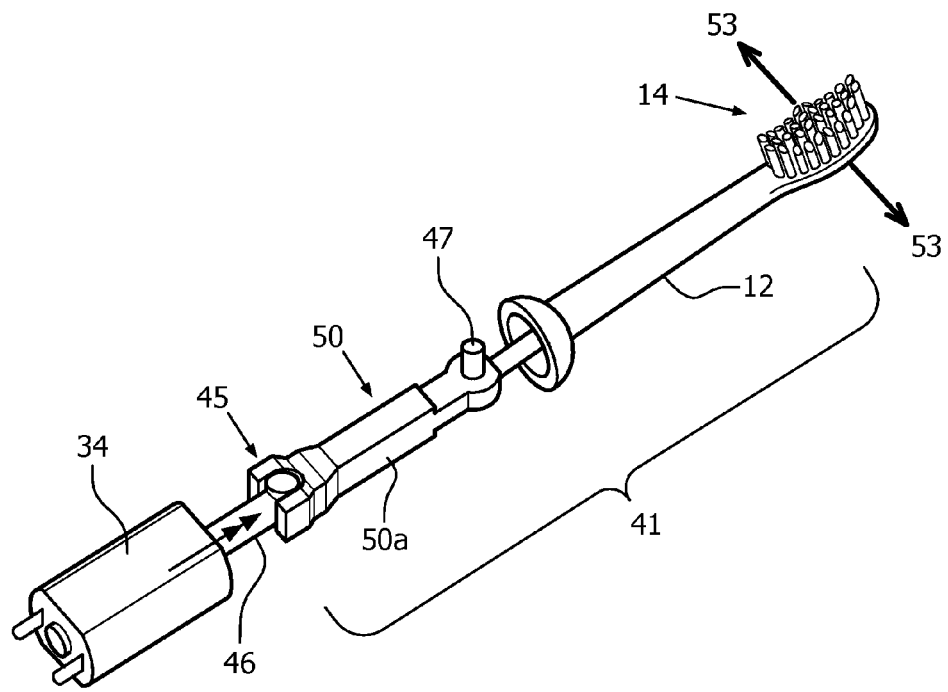
FIGS. 2 and 3 are perspective views showing in more detail the brushhead assembly system of the power toothbrush of FIGS. 1 and 1A.

FIGS. 1 and 1A show a power toothbrush, referred to generally at 10. The power toothbrush 10 includes a brushhead 12 with a brush member 14 at a distal end thereof. Power toothbrush 10 also includes a housing 16 and a chassis assembly 18 which fits inside the housing and which serves as a carrier for several of the internal operating parts of the toothbrush. The rear end of the toothbrush 10 includes an end cap 20, an O-ring seal 22, a tape member 24 and a wire frame member 26, along with an internal cap assembly 28. A conventional battery assembly is shown at 30, with a protective bumper member 32. These portions of the toothbrush 10 are conventional and are common to several power toothbrush arrangements.

Figure 3:
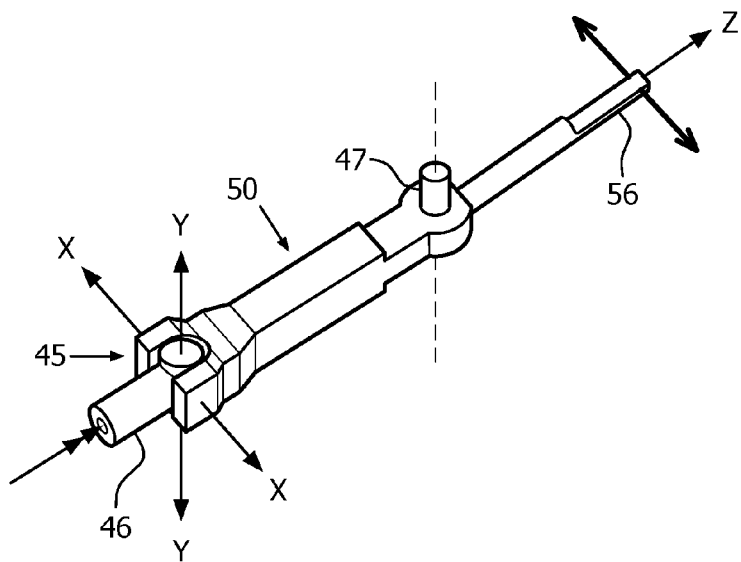

Referring now to FIGS. 1, 2 and 3, a motor 34 is shown, held in place by a motor retainer 36 and attachment screws 38. Positioned on the opposite side of the motor retainer is a printed circuit board 40 containing the control electronics for the toothbrush, along with connecting electrical signal wires 42. In the embodiment shown, motor 34 is a DC motor having an output shaft 44 which rotates and directly produces the torque required to operate the appliance. The motor provides sufficient torque and speed for the drive train to provide the required motion at available battery voltage.

Mounted on the motor output shaft 44 is an eccentric coupling member 46 which produces an eccentric action. The eccentric coupling converts the rotary action of the motor shaft to a circular motion. The center of the eccentric coupling member is offset from the motor shaft axis. When the motor shaft 44 is spinning, the center axis of the eccentric will move in a circular motion, with the diameter of the circle equal to two times the distance of the offset of the eccentric axis from the motor shaft axis. The eccentric coupling is part of a scotch yoke arrangement 45 at the proximal end of the brushhead assembly system. The circular motion produced by the eccentric coupling is converted to a linear (sweeping) motion for a brushhead assembly system 41, which moves about a pivot 47, as shown in FIGS. 2 and 3.

Figure 4:
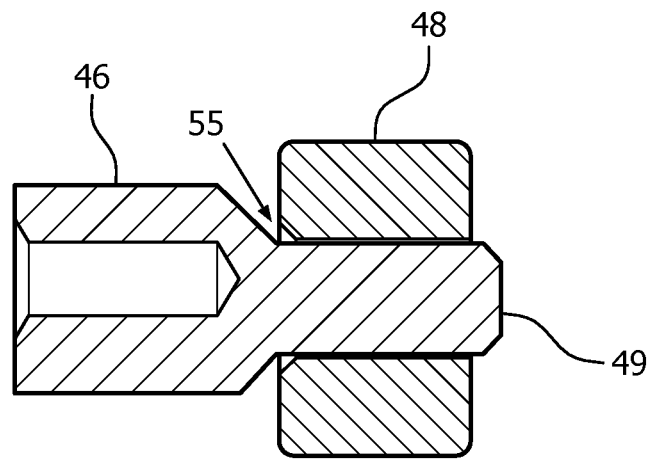
FIGS. 4 and 4A are longitudinal and cross-sectional views of a portion of the power toothbrush of FIGS. 1 and 1A.
Figure 4A:
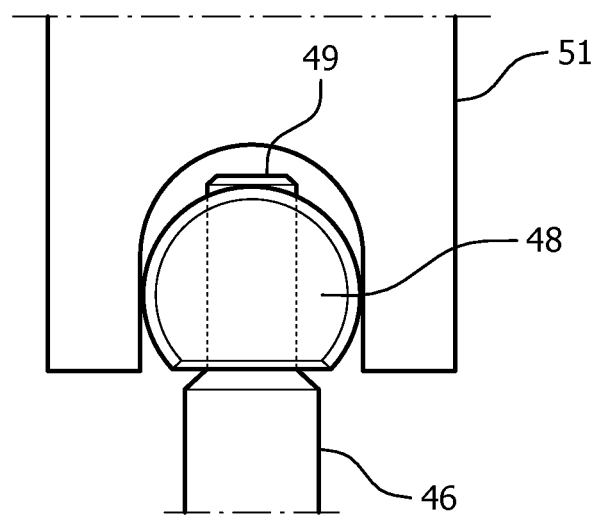

Referring to FIGS. 4 and 4A, at the distal end of the eccentric coupling member 46 is a pin 49 which extends into a cylinder 48 which fits into yoke 51 at the proximal end of the brushhead assembly system. The cylinder 48 is constrained to move basically in the X direction, as shown in FIG. 3, by yoke 51, but is also free to translate to some extent in the Y direction, as well as slightly in the Z direction. The eccentric pin 49 rotates within an opening 55 in cylinder 48. The interface, if too tight, will prevent the eccentric pin from rotating within the cylinder, while if the interface is too loose, the mechanism becomes noisy, and may also affect the amplitude of movement of the brush member 14.

This particular structural arrangement, known generally as a "scotch yoke", is used in the present embodiment to convert the eccentric circular action to a lateral (sweeping) brush assembly action about pivot 47. However, it should be understood that other structural arrangements can be used to produce the desired motion conversion.

The resulting action of the pin 49 acting on cylinder 48 forces yoke 51 in the X direction, transferring the motion of the eccentric coupling to the brushhead assembly system and more particularly to a brushhead drive shaft/beam 50 portion of the brushhead assembly system. The brushhead drive shaft/beam 50 moves laterally back and forth about pivot 47, which is approximately at the center of the overall length of the brushhead assembly system, including brushhead 12, generally extending from yoke 51 to the brush member, which moves in a back-and-forth (lateral) direction about the Y axis, as shown at 53-53 in FIG. 2. The brushhead drive shaft or beam member 50 in the embodiment shown is made from steel. The portion of the beam 50 from the proximal (yoke) end thereof to pivot 47 is covered with a plastic overmoulding 50*a*.

The brushhead 12, with the brush member 14 at a distal end thereof is attachable to and releasable from the distal end portion 56 of the beam 50 by an interference-type fit. Beam 50 is supported by upper and lower cap members 58 and 60. A seal 62 for distal end 56 fits into the distal ends of caps 58 and 60.

In operation, the brushhead assembly system will move in a side-to-side motion. In the arrangement shown, the distance between the yoke 51 and the pivot 47 is approximately one-half of the distance between pivot 47 and brush member 14. As indicated above, brushhead 12 will vary in stiffness, center of gravity and mass, all of which affect the resonant frequency of the brushhead assembly system as it moves in a sweeping motion. Due to the thin geometry and the flexible materials, typically plastic, used in brushhead 12 and the variations thereof, the resonant frequency of the brushhead assembly system will vary between 100-250 Hz, a range which may include the drive frequency of the power toothbrush, as explained above. In some cases, the resonant frequency, depending upon the particular arrangement of the brushhead assembly, can be such relative to the drive frequency, that the resulting amplitude of the brush member is great enough to be uncomfortable.

In the present invention, the resonant frequency of the brushhead assembly system is moved up or down to some degree, in order to mitigate/change the existing resonant frequency of a manufactured system. Desirably, the resulting amplitude of the brush member will be between 1.0-2.5 mm, with a most desired amplitude of 1.75 mm. The resonant frequency of the brushhead assembly system is adjusted by tuning the drive shaft (beam) portion of the brushhead system in three ways, by (1) changing the material of the drive shaft/beam so as to change the stiffness of the beam, (2) changing the length of the beam, and (3) changing the cross-sectional moment of inertia of the beam. As indicated above, the drive shaft/beam 50 extends from a proximal (yoke) end to a point beyond pivot 47. By changing one or more of the above characteristics, the resonant frequency of the brushhead assembly system can be controlled, in order to control the amplitude of the movement of the brush member. This arrangement has the benefit of being able to accomplish a satisfactory yet convenient and inexpensive way to tune the drive shaft and ultimately the brushhead assembly system to permit desired operation of the appliance, without ultra strict control over the manufacturing process, thereby enabling the production of an economical power toothbrush. Typically, the stiffness of the drive train material will be within the range of 10-40 N/mm, the length of the drive train will vary within the range of 45-75 mm, and the cross-sectional moment of inertia will be within the range of 140-280 mm$^4$. One example of such a configured tunable beam which will produce a resonant frequency of 160 Hz with a commercially available brushhead attached, has the following characteristics: beam stiffness 26 N/mm; length 41 mm; cross-section moment of inertia 200 mm$^4$.

While the present invention is used in a direct drive (motor to brush member) arrangement, a pivot action, it can also be applied to other power toothbrush configurations.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A power toothbrush appliance, comprising:
a handle portion which includes a DC motor having a motor shaft;
an eccentric coupling member mounted on the motor shaft; and
a brushhead assembly system, which includes a beam member adapted to receive a removable brushhead with a brush member, wherein the beam member is mounted for lateral movement about a pivot, the lateral movement being accomplished by interaction of the eccentric coupling member with a proximal end portion of the beam member, wherein conversion of a rotational action of the motor shaft to the lateral movement of the beam member is accomplished by a scotch yoke arrangement, and wherein the beam member is tuned via one or more characteristics selected from the group consisting of: (1) a stiffness of the beam member, (2) a length of the beam member and (3) a cross-sectional moment of inertia of the beam member, for changing a resonant frequency of the brushhead assembly system relative to a drive frequency of the power toothbrush appliance to maintain an amplitude of motion of the brush member during operation within a range of 1.0-2.5 mm.

2. The appliance of claim 1, wherein the amplitude of the brush member is maintained at 1.75 mm.

3. The appliance of claim 1, wherein the beam member comprises steel, further having a portion of the beam member from the proximal end thereof to the pivot that comprises a plastic overmoulding.

4. The appliance of claim 1, wherein the lateral movement of the beam member is about a Y axis that is parallel to an axis of the pivot.

5. The appliance of claim 1, wherein a range of stiffness for the beam member is 10-40 N/mm, a range of length for the beam member is 45-75 mm and a range of the moment of inertia for the beam member is 140-280 mm$^4$.

6. The appliance of claim 1, wherein the proximal end of the beam member includes a yoke, and wherein a distance between the yoke and the pivot is one-half of a distance between the pivot and the brush member.

7. The appliance of claim 6, further wherein the beam member comprises steel, and a portion of the beam member from the proximal end thereof to the pivot comprises the steel covered with a plastic overmoulding.

8. A method for implementing a brushhead assembly system portion of a power toothbrush appliance to control a resonant frequency thereof, comprising the steps of:

provSiding a brushhead assembly system that includes a beam portion adapted to receive a brushhead having a brush member, wherein the beam portion undergoes lateral movement about a pivot via a drive system of the power toothbrush appliance, wherein the drive system includes a drive shaft and the lateral movement is accomplished by interaction of an eccentric coupling member mounted on the drive shaft with a proximal end of the beam portion, wherein conversion of a rotational action of the drive shaft to the lateral movement of the beam portion is accomplished by a scotch yoke arrangement, and tuning the beam portion via one or more characteristics of the beam portion so as to maintain a sufficient difference between the resonant frequency of the brushhead assembly system and a drive frequency of the power toothbrush appliance to maintain an amplitude of motion of the brush member in operation within a range of 1.0-2.5 mm, wherein the one or more characteristics are selected from the group consisting of: (1) stiffness of the beam portion; (2) length of the beam portion; and (3) cross-sectional moment of inertia of the beam portion.

9. The method of claim 8, wherein the amplitude of motion of the brush member in operation is maintained at 1.75 mm.

10. The method of claim 8, wherein a range of stiffness for the beam portion is 10-40 N/mm, a range for length of the beam portion is 45-75 mm, and a range of cross-sectional moment of inertia for the beam portion is 140-280 mm$^4$.

11. The method of claim 8, wherein the tuning of the beam portion of the brushhead assembly system is accomplished during manufacture of the power toothbrush appliance.

12. The method of claim 8, wherein providing the brushhead assembly system further includes providing the proximal end of the beam portion with a yoke, and wherein a distance between the yoke and the pivot is one-half of a distance between the pivot and the brush member.

13. The method of claim 12, further wherein the beam portion comprises steel, and a portion of the beam portion from the proximal end thereof to the pivot comprises the steel covered with a plastic overmoulding.

* * * * *